United States Patent [19]

Haust et al.

[11] Patent Number: 4,944,455
[45] Date of Patent: Jul. 31, 1990

[54] AIR TREATING DEVICE

[75] Inventors: Wilhelm M. H. Haust, Toronto; Charles E. Gagnon, Brampton, both of Canada

[73] Assignee: Kinney Canada Inc., Weston, Canada

[21] Appl. No.: 398,537

[22] Filed: Aug. 24, 1989

[51] Int. Cl.⁵ .............................................. A61L 9/04
[52] U.S. Cl. ........................................ 239/59; 239/211
[58] Field of Search ...................... 239/58, 59, 211, 34

[56] References Cited

U.S. PATENT DOCUMENTS

| | | | |
|---|---|---|---|
| 2,481,296 | 9/1949 | Dupuy | 239/59 |
| 2,603,532 | 7/1952 | Wheeler et al. | 239/59 |
| 2,642,310 | 6/1953 | Meek et al. | 239/59 |
| 2,708,138 | 5/1955 | Gooken | 239/59 |
| 2,738,225 | 3/1956 | Meek | 239/59 |
| 3,633,538 | 1/1972 | Hoeflin | 239/34 |
| 4,258,004 | 3/1981 | Valenzona et al. | 239/59 |
| 4,361,279 | 11/1982 | Beacham | 239/58 |
| 4,549,693 | 10/1985 | Barlics | 239/58 |
| 4,630,775 | 12/1986 | Mandon et al. | 239/59 |

FOREIGN PATENT DOCUMENTS

| | | | |
|---|---|---|---|
| 560143 | 3/1975 | Switzerland | 239/59 |
| 1379679 | 1/1975 | United Kingdom | 239/59 |

Primary Examiner—Andres Kashnikow
Assistant Examiner—Michael J. Forman
Attorney, Agent, or Firm—Abelman Frayne Rezac & Schwab

[57] ABSTRACT

This invention relates to an air treating device. Two halves of a hollow ball are connected. A rotatable ring is provided which has an aperture which in one position is sealed and in another open to release volatilizable material. The halves may be connected by a post upon which a donut shaped disc of fragrant material can be mounted.

3 Claims, 2 Drawing Sheets

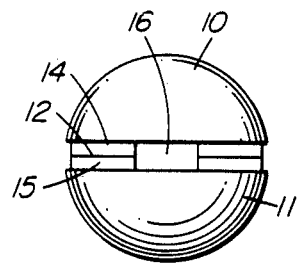
FIG. 1
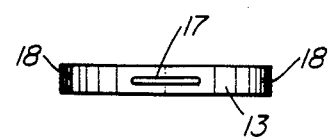
FIG. 2
FIG. 3
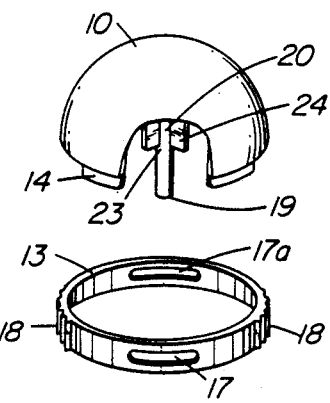
FIG. 5
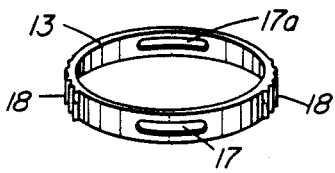
FIG. 6
FIG. 4
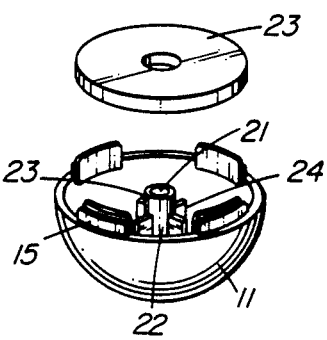
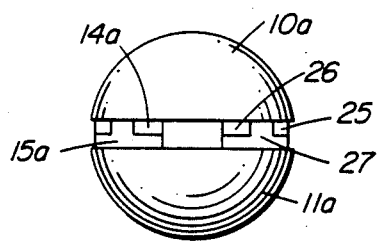
FIG. 7

AIR TREATING DEVICE

This invention relates to an air treating device.

One of the air treating devices on the market under the trademark "Sneaker Balls" is in the shape of a small ball of a size suitable for insertion into a sneaker. The ball is formed from two hemispheres between which a removable ring is located. A disc of a volatilizable air treating compound is placed loosely within the ball and the ring acts as a seal to prevent premature volatilization of the air treating compound. The user must separate the hemispheres, remove the ring and then reassemble the hemispheres to use the item. If it is desired to seal the ball, the ring, which may by then have been lost, must be replaced.

A disadvantage of the foregoing construction is the inconvenience of disassembling and reassembling the conponents to remove or replace the sealing ring.

A further disadvantage is that these small balls are attractive to children who may easily open them. Some air treating compounds are toxic if eaten by a small child.

Another disadvantage is that the air freshening compounds are placed loosely within the balls where they rattle around and also are not located in the best position for utilization.

The object of this invention is to overcome the foregoing disadvantages.

The invention is based on the idea of connecting the two halves of a hollow ball containing the volatilizable material firmly together, and providing a rotatable ring into an aperture. In one position of the ring the aperture is open to release the volatilizible material. In another position it is sealed. The halves may conveniently be connected by a post which is axial to the axis of rotation of the ring and this post provides a convenient mounting for donut shaped discs of fragrant material.

This invention in one aspect more specifically provides an air treating device comprising two interacting bodies joining along a circular join line to provide a hollow container for a volatilizable air treating compound, a rotatable annular ring at the circular join line, said annular ring having at least one aperture for the passage of volatilized air treating compound, means disposed interiorly of said annular ring to provide an opening in register with said aperture at one position of the annular ring and for sealing said aperture at another position of the annular ring and means for connecting said bodies together to prevent easy access to the volatilizable air treating compound.

In a preferred aspect a post is provided extending axially with respect to the axis of rotation of the annular ring to suspend a donut shaped disc of volatilizable air treating compound substantially in the plane of the rotatable disc.

In the drawings which illustrate the preferred embodiments of this invention:

FIG. 1 is an elevation view of the two interacting hollow bodies without the rotatable ring;

FIG. 2 is an elevation view of a rotatable ring to be used with FIG. 1;

FIG. 3 is a perspective view partly broken away of one of the two interacting hollow bodies;

FIG. 4 is a perspective view of the other of the two interacting hollow bodies;

FIG. 5 is a perspective view of the ring to be used with the hollow bodies of FIGS. 3 and 4;

FIG. 6 is a perspective view of a donut shaped disc of volatilizable air treating compound;

FIG. 7 is an elevation view similar to FIG. 1 of an alternative embodiment;

Figure 8:
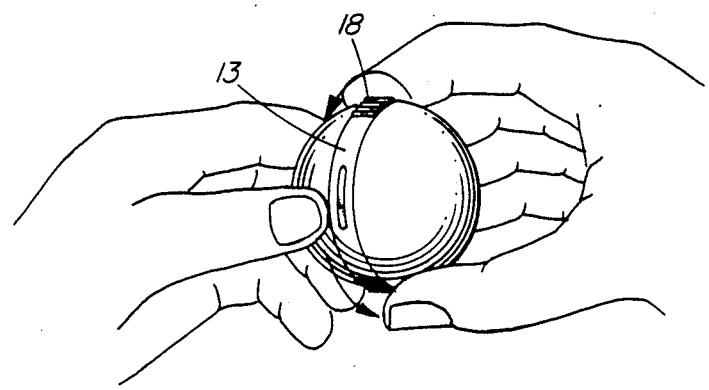
FIG. 8 is a perspective view illustrating the use of an air treating device in accordance with this invention.

Referring now the FIGS. 1 to 4, the air treating device illustrated comprises a first hollow body 10 and a second hollow body 11 joining along join line 12. A rotatable annular ring 13 illustrated in FIGS. 2 and 5 is located at the join line. Body 10 has projections 14 which abut similar projections 15 on body 11 to provide a seat for rotatable ring 13. The pairs of projections 14 and 15 are spaced to leave openings 16. Ring 13 has diametrically opposed apertures 17 and 17a which at one position of ring 13 are in alignment with openings 16 and at another position of ring 13 are sealed by projections 14 and 15. Projections 14 and 15 should be arranged so that both apertures 17 and 17a are either open to release the volatilizable air treating material or closed. Preferably ring 13 has knurled sections 18 to facilitate rotation of the annular ring.

Hollow bodies 10 and 11 are joined together by providing a pin and socket connection or other suitable means. For example, body 10 has a pin 19 mounted on prong 20 which engages with socket 21 which is within prong 22. Prongs 20 and 22 combine to provide a supporting post 23 which a donut shaped pad of air freshening material may be mounted. In order to make the device child resistant, pin 19 may be cemented into socket 21 or some other connection may be used such as by providing pin 19 with an enlarged head and undercutting socket 21. Prongs 20 and 22 extend internally from the centres of the hemispherical hollow bodies 10 and 11 and have flutes 24 which not only give post 23 additional stability but maintain pad 23 substantially in the plane of ring 13 so that air flowing through one of holes 17 and 17a to the other flows across the surface of pad 23. Pad 23 is therefore located in an optimum position for the purpose fo achieving volatilization from both surfaces.

Pad 23 may be of paper, cardboard or sponge impregnated or coated with conventional air freshening and/or odour treating ingredients of a volatilizable nature.

FIG. 7 illustrates an alternative embodiment in which projections 14a extending from body 10a are recessed as illustrated to leave a pair of projections 25 and 26 to receive a prong 27 in interlocking fashion extending from projection 15a. This interlock may help strengthen the structure and make it more child resistant. It will be appreciated that it is virtually impossible to provide a structure that is completely childproof to a determined child. Nevertheless, it is an important advantage to provide resistance to easy access.

As shown in FIG. 8, ring 13 is rotated by hand so that apertures 17 and 17a are in alignment with the hole 16 to permit volatilizable deodorizing or air freshening material to escape. It may also quickly be rotated to a sealed position in which apertures 17 and 17a are aligned with projections 14 and 15. This not only provides an advantage when the device is initially placed into use. It enables the life and potency of the air freshening material to be extended by easily closing off apertures 17 and 17a when freshening or deodorizing is not required.

Figure 9:
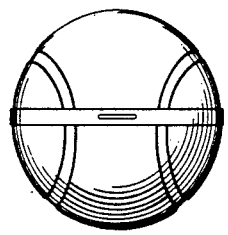
FIGS. 9 to 12 are elevation views illustrating air treating devices simulating various miniature game balls.
Figure 10:
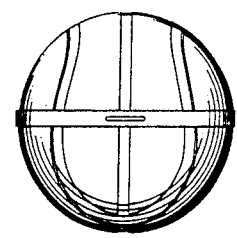
Figure 11:
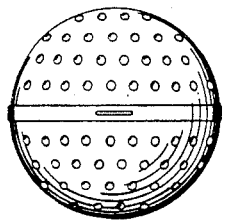

FIG. 9 shows a representation of a tennis ball. FIG. 10 is intended to simulate a basket ball and FIG. 11 a golf ball. Each of the balls illustrated in FIGS. 9, 10 and 11 may, for example, be about 38 mm. in diameter.

Figure 12:
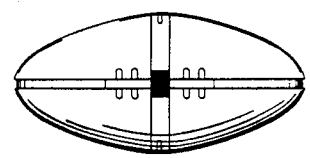

FIG. 12 shows a representation of a football with a minimum diameter of 25 mm. and a length of 50 mm.

A further advantage of a structure in accordance with this invention is that retaining the ring as part of a ball of the type shown in FIGS. 9 to 12, as compared with a structure in which the ring is removed, helps to retain the appearance of a game ball.

It is claimed:

1. An air treating device comprising first and second interacting bodies joining along a circular join line to provide a hollow container for a volatilizable air treating compound, said join line being in a unitary plane, a rotatable annular ring having at least two apertures for the passage of volatilized air, said annular ring being mounted about said hollow body for rotation in said unitary plane, means disposed interiorly of said annular ring to provide openings in said hollow body in register with said apertures at one position of rotation of the annular ring and for sealing said apertures at another position of rotation of the annular ring, a post for connecting said bodies together, said post including a male post section joined to the first interacting body and a female post section joined to the second interacting body, said male and female post sections cooperating when engaged to provide a post extending substantially axially with respect to the axis of rotation of said ring, said male and female post sections being connected sufficiently securely to prevent easy access to the hollow container, a donut shaped disc of volatilizable material having upper and lower surfaces mounted on said post substantially in said unitary plane whereby air will flow freely between at least two apertures over both said upper and lower surfaces of the disc.

2. An air treating device as in claim 1, in which the male and female post sections are each fluted to strengthen such sections and to support said disc in said unitary plane.

3. An air treating device as in claim 1 in which the hollow bodies simulate a miniature game ball of a size suitable for insertion within running shoes.

* * * * *